(12) United States Patent
Cirka et al.

(10) Patent No.: US 9,423,333 B2
(45) Date of Patent: Aug. 23, 2016

(54) METHODS AND SYSTEMS FOR VISCOELASTIC CHARACTERIZATION OF IRREGULARLY SHAPED ANISOTROPIC BIOLOGICAL SAMPLES

(75) Inventors: Heather A. Cirka, Manchester, NH (US); Kristen L. Billiar, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 401 days.

(21) Appl. No.: 14/003,266

(22) PCT Filed: Mar. 27, 2012

(86) PCT No.: PCT/US2012/030652
§ 371 (c)(1),
(2), (4) Date: Dec. 16, 2013

(87) PCT Pub. No.: WO2012/135165
PCT Pub. Date: Oct. 4, 2012

(65) Prior Publication Data
US 2014/0102180 A1    Apr. 17, 2014

Related U.S. Application Data

(60) Provisional application No. 61/470,872, filed on Apr. 1, 2011.

(51) Int. Cl.
*G01N 11/14* (2006.01)
*G06T 7/00* (2006.01)
*G06T 7/60* (2006.01)

(52) U.S. Cl.
CPC .............. *G01N 11/14* (2013.01); *G06T 7/0004* (2013.01); *G06T 7/606* (2013.01); *G01N 2203/0089* (2013.01); *G01N 2203/0094* (2013.01); *G06T 2207/30164* (2013.01)

(58) Field of Classification Search
CPC ...................................................... G01N 11/14
USPC ............ 73/54.23, 54.27–54.29, 54.33, 54.39; 356/72
See application file for complete search history.

(56) References Cited

U.S. PATENT DOCUMENTS

| | | | | |
|---|---|---|---|---|
| 4,878,379 A * | 11/1989 | Deer | ...................... | G01N 11/10 374/46 |
| 5,349,847 A * | 9/1994 | Lee | ...................... | G01N 11/142 73/54.28 |
| 5,763,766 A * | 6/1998 | Robinson | ............... | G01N 11/14 73/54.28 |
| 5,777,212 A * | 7/1998 | Sekiguchi | ............ | G01N 11/162 73/54.33 |
| 6,666,073 B2 * | 12/2003 | Sentmanat | ........... | G01N 11/162 73/54.28 |
| 7,441,442 B2 * | 10/2008 | Morgan | .............. | F16C 32/0446 73/54.28 |

(Continued)

OTHER PUBLICATIONS

Kragel et al, Interfacial shear rheology of protein-surfactant layers, Advances in Colloid and Interface Science 144 (2008) 38-53, Progress in Polymer Science.*

(Continued)

*Primary Examiner* — Hezron E Williams
*Assistant Examiner* — Hoang Nguyen
(74) *Attorney, Agent, or Firm* — Burns & Levinson LLP; Orlando Lopez

(57) ABSTRACT

Methods that extend the utility of standard rotational rheometers for accurate and sensitive viscoelastic characterization of small or small irregularly shaped or small anisotropic samples and systems to implement those methods.

13 Claims, 7 Drawing Sheets

(56) References Cited

U.S. PATENT DOCUMENTS

2003/0171849 A1 9/2003 Martin
2007/0266776 A1* 11/2007 Liberatore ........... G01N 11/142
  73/54.23
2009/0133478 A1* 5/2009 Sentmanat ............. G01N 11/14
  73/54.28

OTHER PUBLICATIONS

Hyun et al., A Review of Nonlinear Oscillatory Shear Tests: Analysis and Application of Large Amplitude Oscillatory Shear (LAOS), Jan. 2011.*

Ravindranath et al., Large Am_plitude Oscillatory Shear Behavior of Entanglecf Polymer Solutions: Particle Tracking Velocimetric Investigation, University of Akron Main Campus, College of Polymer Science and Polymer Engineering, May 2008.*

International Search Report and Written Opinion dated Jul. 9, 2012 for PCT/US12/30652.

Cirka, H.A. et al. Eccentric Rheometry for Viscoelastic Characterization of Small, Soft, Anisotropic, and Irregularly Shaped Biopolymer Gels and Tissue Biopsies. Annals of Biomedical Engineering ((c)2012). Published online: Feb. 24, 2012 (12 pgs).

* cited by examiner

METHODS AND SYSTEMS FOR VISCOELASTIC CHARACTERIZATION OF IRREGULARLY SHAPED ANISOTROPIC BIOLOGICAL SAMPLES

CROSS-REFERENCE TO RELATED APPLICATIONS

This application is a U.S. national stage application under 35 U.S.C. 371 of International Application No, PCT/US12/30652 filed on Mar. 27, 2012 and entitled METHODS AND SYSTEMS FOR VISCOELASTIC CHARACTERIZATION OF IRREGULARLY SHAPED ANISOTROPIC BIOLOGICAL SAMPLES, which in turn claims priority to U.S. Provisional Patent Application No. 61/470,872 filed on Apr. 1, 2011, which is incorporated by reference herein in its entirety for all purposes.

BACKGROUND

This invention relates generally to viscoelastic characterization of samples, and, more particularly, to one.

Quantification of the viscoelastic properties of soft tissue biopsies and fibrous protein gels is vital to the understanding of normal tissue development, wound healing, disease progression, and cell-mediated remodeling engineered tissues (e.g., collagen, fibrin). Rheometers are theoretically well suited for characterizing the storage and loss modulus of such soft gels; however, standard "geometries" used in such commercial instruments require relatively large, homogeneous samples to generate sufficient torque for accurate analysis of low stiffness materials. Additionally, the analysis generally assumes isotropic linear viscoelastic behavior. Newly formed tissues and biological protein gels such as blood clots are often small, soft, irregularly shaped, anisotropic, and difficult to handle. Rheometry of tissue samples and other biological samples, such that the results of biopsies, is not common in the literature since the samples are not compatible with the conventional rheometers used in the conventional manner.

There is a need for methods that extend the utility of standard rotational rheometers for accurate and sensitive viscoelastic characterization of small, irregularly shaped biological samples.

BRIEF SUMMARY

Methods that extend the utility of standard rotational rheometers for accurate and sensitive viscoelastic characterization of small or small irregularly shaped or small anisotropic samples and systems to implement those methods are disclosed hereinbelow.

In one or more embodiments, the method of these teachings for viscoelastic characterization of small samples includes locating a sample so that the sample is radially offset from a center of a sample holding section of a conventional parallel plate rotational rheometer, obtaining geometrical and location properties of the sample, obtaining, from the geometrical and location properties of the sample, a polar moment of inertia for the sample and obtaining, from a complex modulus of elasticity obtained from the conventional parallel plate rotational rheometer, using the polar moment of inertia for the sample, a complex modulus of elasticity for the sample.

In one or more embodiments, the system of these teachings for viscoelastic characterization of small samples includes a holding component configured such that a sample is radially offset from a center of a sample holding section of a conventional parallel plate rotational rheometer and configured to provide the sample to the conventional parallel plate rotational rheometer, an imaging component configured to acquire an image of the sample, an analysis component adapted to obtain, from the geometrical and location properties of the sample, a polar moment of inertia for the sample and an adjustment component adapted to obtain, from a complex modulus of elasticity obtained from the conventional parallel plate rotational rheometer, using the polar moment of inertia for the sample, a complex modulus of elasticity for the sample.

Other embodiments of the method and system of the teachings also disclosed.

For a better understanding of the present teachings, together with other and further objects thereof, reference is made to the accompanying drawings and detailed description and its scope will be pointed out in the appended claims.

DETAILED DESCRIPTION

The following detailed description is of the best currently contemplated modes of carrying out these teachings. The description is not to be taken in a limiting sense, but is made merely for the purpose of illustrating the general principles of these teachings, since the scope of these teachings is best defined by the appended claims.

The present teachings will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

The following configuration description is presented for illustrative purposes only. Any computer configuration and architecture satisfying the speed and interface requirements may be suitable for implementing the system and method of the present embodiments.

To assist in the understanding of the present teachings the following definitions are presented:

"Modulus of elasticity," also referred to as modulus, as used herein, refers to a measure of dynamic mechanical properties of a material. If the measure takes into account energy dissipated as heat during deformation and recovery (the loss modulus), the modulus is referred to as the complex modulus.

"Polar moment of inertia," as used herein, is a measure of an object's ability to resist torsion and is given, mathematically, by an integral over an area.

Figure 1:
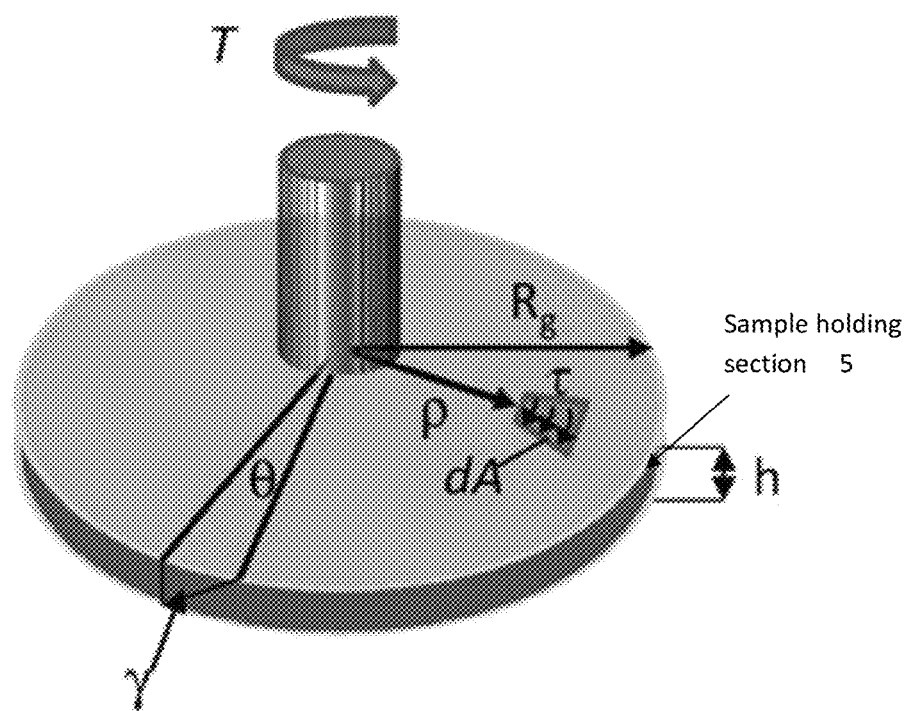
FIG. 1 is a schematic graphical representation of a conventional parallel plate rotational rheometer.

Conventional parallel plate rotational rheometers, such as shown in FIG. 1 (where the sample holding section 5 is the section including the parallel plates separated by the distance h), apply a torque, T, which, at least for small amplitudes, is related to the complex modulus of the sample being tested by:

$$T(t) = G^* \frac{\theta(t)}{h} \int_A \rho^2 dA = G^* \frac{\theta(t)}{h} J \quad (1)$$

where $G^*$ is the complex modulus, $\theta$ is the angle of rotation (linearly related to strain), h is the gap height, $\rho$ is the radius from the axis of rotation to an incremental area, dA, and J is the polar moment of inertia, defined by the integral in (1). For a circular sample with radius r, undergoing a rotation about its center, the polar moment of inertia is:

$$J_0 = \pi \frac{r^4}{2} \quad (2)$$

Conventional rheometric software assumes that the sample is centered (i.e., d=0).

In one or more embodiments, the method of these teachings for viscoelastic characterization of small samples includes locating a sample so that the sample is radially offset from a center of a sample holding section of a conventional parallel plate rotational rheometer, obtaining geometrical and location properties of the sample, obtaining, from the geometrical and location properties of the sample, a polar moment of inertia for the sample and obtaining, from a complex modulus of elasticity obtained from the conventional parallel plate rotational rheometer, using the polar moment of inertia for the sample, a complex modulus of elasticity for the sample.

While some of the embodiments described hereinbelow apply to at least small amplitude analysis, it should be noted that these teachings can also be applied to Large Amplitude Oscillatory Shear analysis (see for example, Hyun, K., Wilhelm, M., Klein, C. O., Cho, K. S., Nam, J. G., Ahn, K. H., Lee, S. J., Ewoldt, R. H. and McKinley, G. H., A Review of Nonlinear Oscillatory Shear Tests: Analysis and Application of Large Amplitude Oscillatory Shear (LAOS), Rev. Poly. Sci, (2010) 36, 1697-1753, which is incorporated by reference herein in its entirety and for all purposes).

These teachings extend the application of a conventional parallel plate rotational rheometers to small samples such as, but not limited to, soft tissue biopsies and pre-polyamide gel samples.

In one instance, the sample is located in a radially offset position by placing the sample on a holding component, the sample being placed so that the sample is radially offset from the center of the sample holding section of the conventional parallel plate rotational rheometer. In one embodiment, the sample holding component is a glass slide.

In one instance, the geometrical and location properties of the sample are obtained by obtaining an image of the sample while placed on the holding component and obtaining the geometrical and location properties of the sample from the image. The geometrical and location properties can include position, size and shape.

The moment of inertia of the sample is obtained by evaluating the integral in (1) over the area of the sample. In one embodiment, other embodiments also being within the scope of these teachings, the image of the sample is pixilated, thresholded and converted to binary with the sample area having a value of 1 and the background area having a value of 0. In one integration approximation, the moment of inertia of the sample is calculated as the sum of each pixel multiplied by the square of the distance from the axis of rotation to that pixel. It should be noted that other integration approximations are within the scope of these teachings.

In one embodiment, the modulus of elasticity for the sample is obtained by adjusting the modulus of elasticity obtained from the conventional parallel plate rotational rheometer by the ratio of a polar moment of inertia for a test sample that occupies the sample holding section of the conventional parallel plate rotational rheometer from the center to an outer radius of a location of the sample to the polar moment of inertia for the sample. That is, the modulus value output from the rheometer analysis software, $G_{rheo}^*$ is multiplied by a correction factor, b. The correction factor b is the ratio of $J_s$, the polar moment of inertia of the sample, and $J_{rheo}$, the polar moment of inertia that the sample would have if it filled the entire area under the geometry. The correction factor, at least for small amplitude analysis, is obtained by rearranging the terms in Eq. (1):

$$\frac{T}{\theta} h = G_{rheo}^* J_{rheo} = G_s^* J_s \quad (3)$$

Further rearrangement yields:

$$G_s^* = \frac{J_{rheo}}{J_s} G_{rheo}^* = b G_{rheo}^* \quad (4)$$

$J_{rheo}$ is calculated using Eq. (2) with $r=R_g$ where $R_g$ is calculated by fitting a number of user-selected points on the edge of the geometry in image described above (prethresholding but after pixilation) to the equation for a circle.

In another embodiment, the method disclosed herein above is performed at various orientations (relative to the direction of loading) in order to consider anisotropy of the sample.

In one or more embodiments, the system of these teachings for viscoelastic characterization of small samples includes a holding component configured such that a sample is radially offset from a center of a sample holding section of a conventional parallel plate rotational rheometer and configured to provide the sample to the conventional parallel plate rotational rheometer, an imaging component configured to acquire an image of the sample, an analysis component adapted to obtain, from the geometrical and location properties of the sample, a polar moment of inertia for the sample and an adjustment component adapted to obtaining, from a complex modulus of elasticity obtained from the conventional parallel plate rotational rheometer, using the polar moment of inertia for the sample, a complex modulus of elasticity for the sample.

In one instance, the holding component comprises a substantially flat piece of a substantially transparent material dimensioned to be located in the sample holding section of the conventional parallel plate rotational rheometer; and a rod located at substantially the center of substantially flat piece, the rod being adapted to be placed in the sample holding section of the conventional parallel plate rotational rheometer. In one embodiment, the substantially flat piece has an etched portion.

In one instance, the imaging component includes an image acquisition component and optical components disposed between the sample and the image acquisition component, the optical components being configured to provide an image of the sample to the image acquisition component. In one embodiment, the optical components include a prism disposed to receive an image of the sample and provide the image to the image acquisition component. The imaging component facilitates viscoelastic characterization of irregularly shaped samples, such as, for example, tissue biopsies and discarded clinical tissue samples. The imaging component also enables obtaining the samples in their natural state.

Figure 2A:
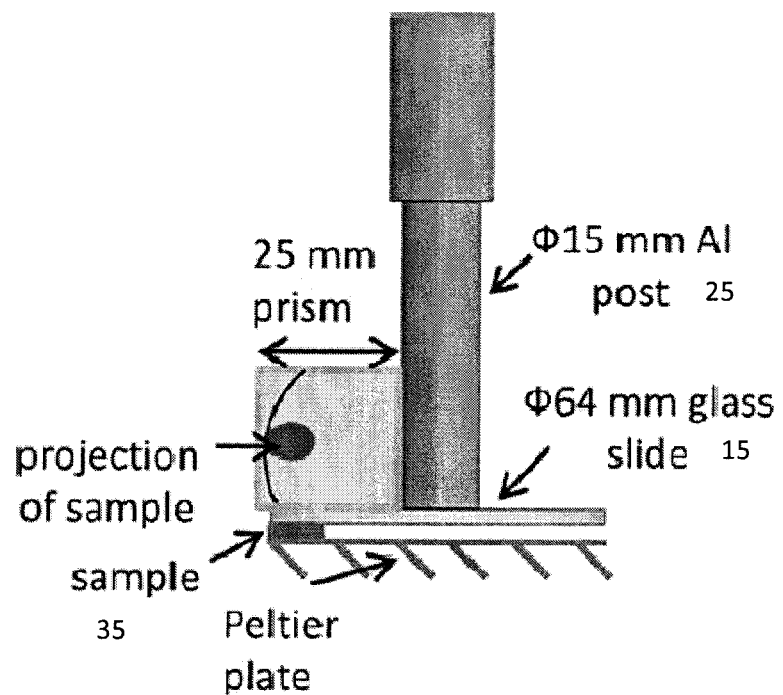
FIGS. 2a and 2b our schematic graphical representations of components of the system of these teachings.
Figure 2B:
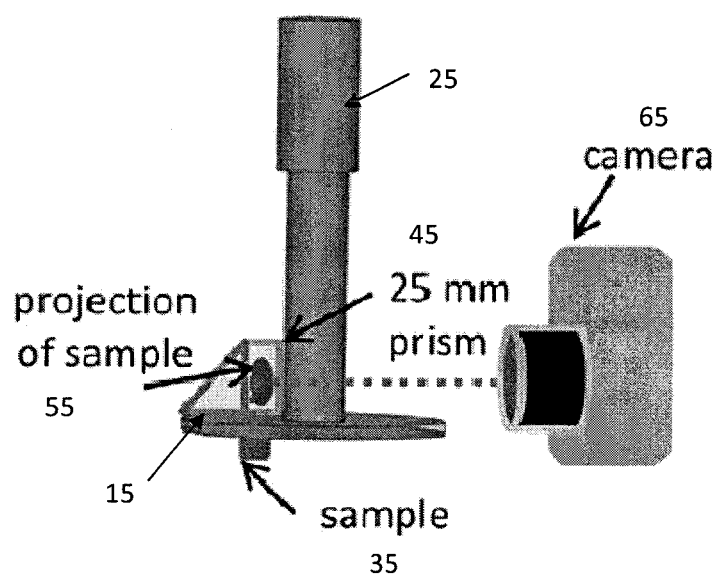

FIGS. 2a and 2b show components of an exemplary embodiment of the system of these teachings. Referring to FIG. 2a, in the exemplary embodiment shown therein, a rheometer attachment includes a glass slide 15 affixed to an aluminum post 25. In one instance, the glass slide 15 has an etched portion on which the sample 35 is positioned. Referring to FIG. 2b, in the exemplary embodiment shown therein, a prism 45 is disposed on the glass slide 15 so that the prism 45 provides a projection 55 of the sample 35. The prism 45 (an orthogonal prism in the embodiment shown) is optically configured to provide the projection 55 of the sample to an image acquisition component 65 (a camera in the embodiment shown).

It should be noted that these teachings are not limited only to the exemplary embodiments disclosed hereinabove and hereinbelow.

In one embodiment, the analysis component includes one or more processors, the one or more processors being operatively connected to the imaging component and receiving an image of the sample from the imaging component, and computer usable media having computer readable code embodied therein, the computer readable code causing the one or more processors to obtain the polar moment of inertia for the sample.

In another embodiment, the computer readable code also causes the one or more processors to obtain a radius for a test sample, the radius being obtained from a number of selected locations on a periphery of the image of the sample.

In still another embodiment, the adjustment component can also be constituted by the one or more processors and the computer usable media having computer readable code that causes the one or more processors to obtain of a polar moment of inertia for the test sample and adjust the modulus of elasticity obtained from the conventional parallel plate rotational rheometer by the ratio of the polar moment of inertia for the test sample to the polar moment of inertia for the sample.

Figure 3A:
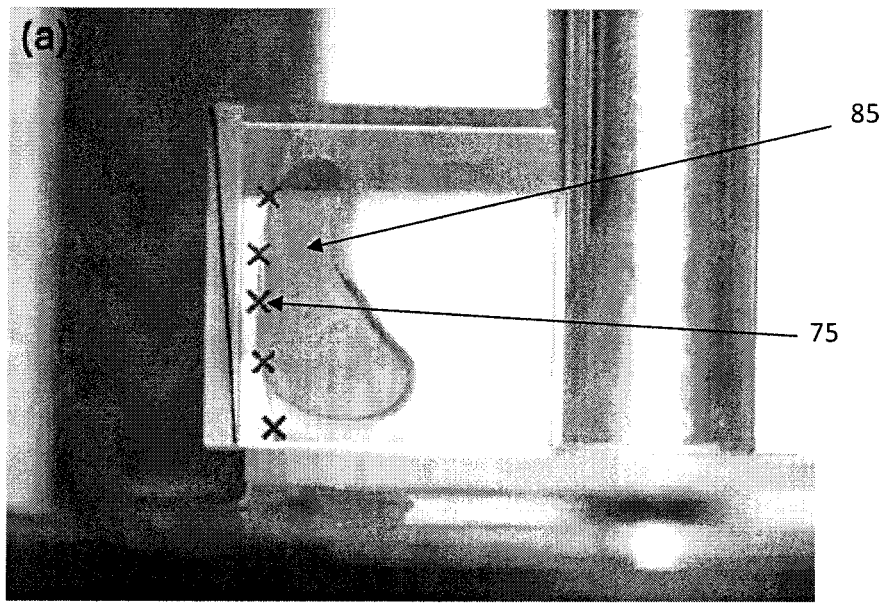
FIG. 3a is a pictorial representation of an image and points used to obtain a quantity of interest in an embodiment of these teachings.

In one exemplary embodiment, shown in FIG. 3a, $R_g$, the radius used in Eq. (2) for calculating $J_{rheo}$, is calculated by fitting a number of user-selected points 75 (five in the embodiment shown) on the edge of the geometry 85 in the image described above (prethresholding but after pixilation) to the equation for a circle.

Figure 3B:
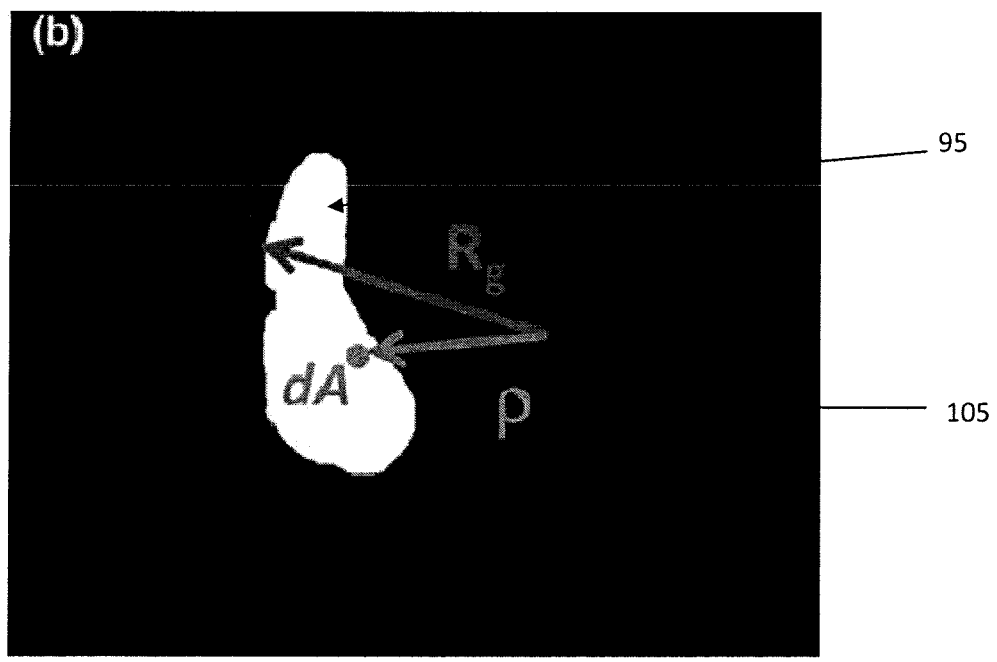
FIG. 3b is a pictorial representation of an image used to obtain another quantity of interest in an embodiment of these teachings.

In another exemplary embodiment, shown in FIG. 3b, the image of the sample is pixilated, thresholded and converted to binary with the sample area 95 having a value of 1 and the background area 105 having a value of 0. In one integration approximation, the moment of inertia of the sample is calculated as the sum of each pixel multiplied by the square of the distance from the axis of rotation to that pixel. It should be noted that other integration approximations are within the scope of these teachings.

Figure 4:
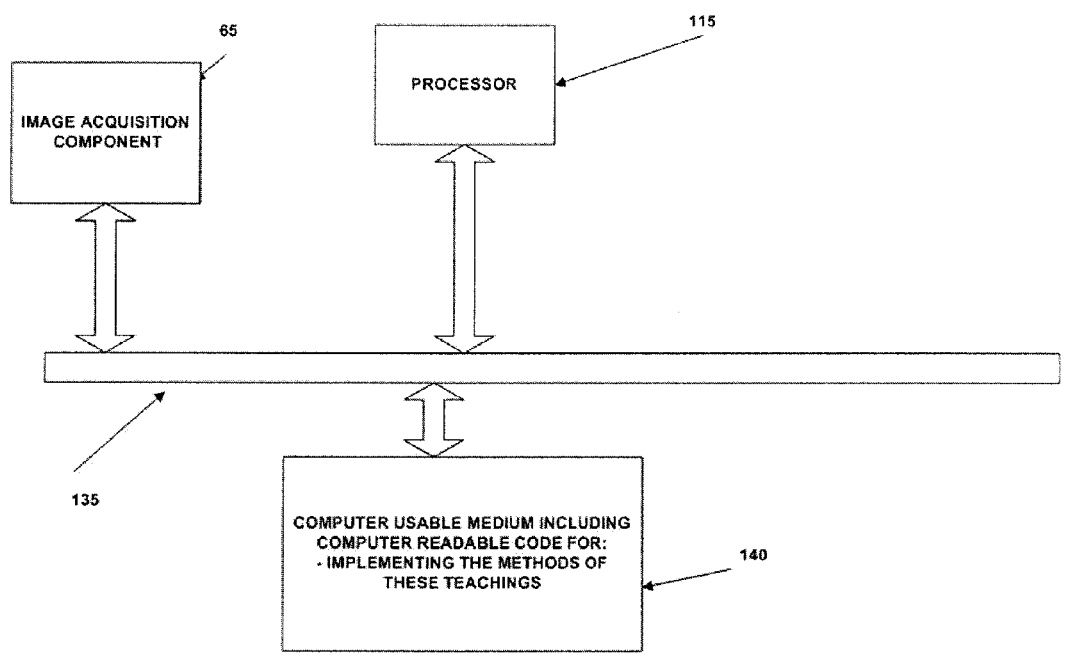
FIG. 4 is a schematic representations of components in one embodiment of the system of these teachings.

FIG. 4 shows one embodiment of the analyses and adjustment components in the embodiment of the system disclosed hereinabove. Referring to FIG. 4, the image acquisition components 65 provides image data to the one or more processors 115 and the computer usable media 140 has computer readable code that causes the one or more processors 115 to implement the method of these teachings as disclosed hereinabove. The image acquisition component 65, the one or more processors 115 and the computer usable media 140 are operatively connected by a connection component 135 (such as a computer bus).

EXEMPLIFICATION

In order to further elucidate these teachings, an exemplary embodiment is disclosed herein below and results obtained from the exemplary embodiment also disclosed. It should be noted that these teachings are not limited to only the exemplary embodiment.

In one exemplary embodiment, a transparent circular geometry was formed from a $\phi 64$ mm glass slide which allows direct visualization of the sample. The glass slide (15, FIG. 2a) was attached to an aluminum rod (25, FIG. 2a) that interfaces with a standard rotational rheometer (for example, but not limited to, a model inAR-G2, TA instruments, New Castle, Del.). The glass slide ($\phi 64$ mm) 15 was etched using dilute hydrofluoric acid (in one exemplary instance, for 24 hours) to ensure adequate friction between geometry and sample in order to reduce slippage during testing. In the exemplary embodiment, the etched glass slide 15 was affixed to the center of the aluminum rheometer attachment with epoxy glue.

A combination of an orthogonal prism 45 and high resolution camera 65 were used to capture the image 55 of the projected surface of the sample and the edge of the geometry as shown in FIG. 2b. After rheological measurements, the prism was placed just above (without touching) the clear glass geometry using a custom jig. Alignment gigs were also be used to ensure that the camera and the prism remain aligned.

A custom MATLAB (Mathworks, Natick, Mass.) program was created for analysis of the image of the sample and geometry. The image was thresholded and converted to binary with the sample becoming white (value of one) and all else black (value of zero) as shown in FIG. 3b. Sample moment of inertia, $J_s$, was calculated as the sum of the product of the value of each pixel and the square of distance from the axis of rotation to that pixel.

Figure 5A:
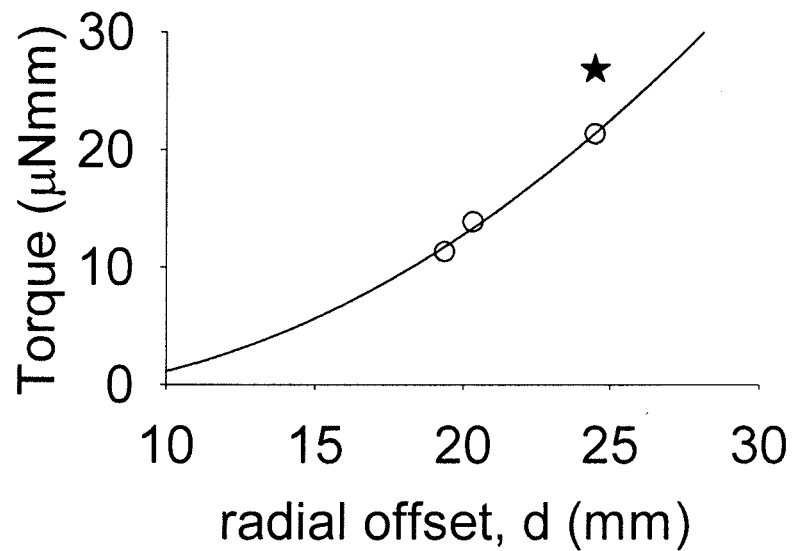
FIGS. 5a and 5b show results obtained using an embodiment of the method of these teachings.
Figure 5B:
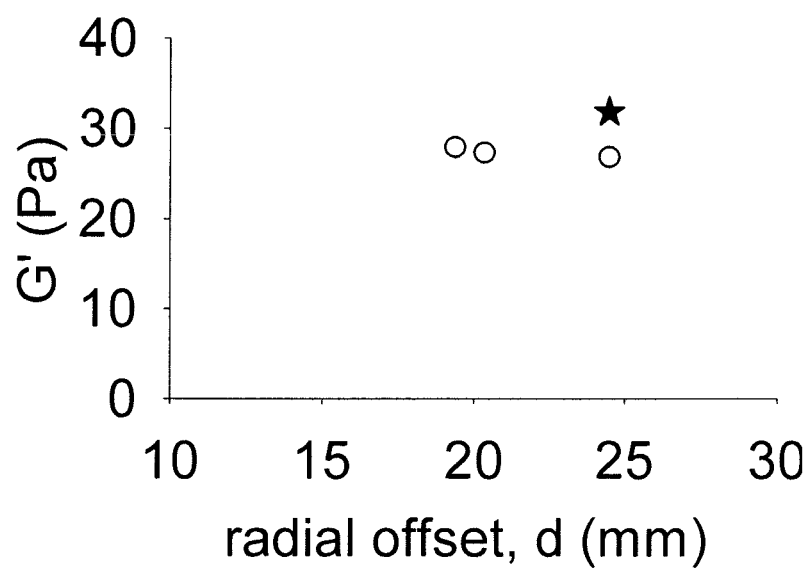

To demonstrate the increase in torque with increasing offset, and the insensitivity of the calculated $G'_s$ to the offset, samples were moved radially outwards from the center of rotation. FIG. 5a shows the increase in torque as the sample is placed at greater radial distances. FIG. 5b shows $G'_s$ calculated data in 'a' demonstrating independence of radial offset and shape. (Irregular samples are indicated with a star.) $G'_s$ was calculated with MATLAB using Eqn. 4 (FIGS. 5a, 5b); only the storage modulus (G') is reported since the loss modulus (G") is <0.1G'. Further, to demonstrate the ability to obtain an accurate measure of G' for irregular-shaped samples, the samples were cut in half and the semicircles rotated to form an odd shape. The values for the irregular shapes were within the 3% error (although it appears slightly higher in FIGS. 5a, 5b as indicated by the star).

Figure 6:
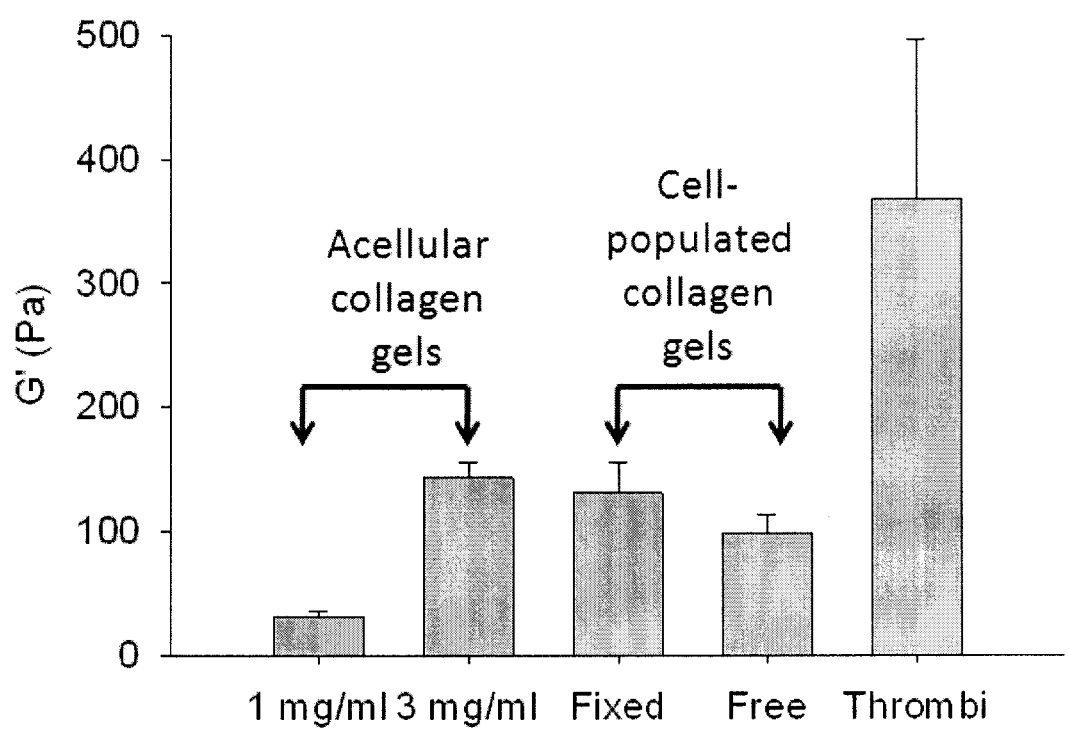
FIG. 6 shows the results obtained for small irregular shapes using an embodiment of the method of these teachings.

To demonstrate the broad applicability of this method, φ15 mm a cellular collagen gels in two concentrations, cell remodeled gels (both with boundaries anchored and free floating) as well as thrombi samples were tested. FIG. 6 shows the storage modulus for various protein gels (mean±SD). A cellular collagen gels are 1 and 3 mg/ml of acid-extracted rat tail collagen polymerized in a φ15 mm culture dish. Cell-populated collagen gels were 2 mg/ml collagen with 1 million cells/ml initial concentration, cultured for 22 hrs freely floating (Free) or rigidly attached (Fixed) to the culture substrate. Model thrombi were made from porcine blood coagulated with $CaCl_2$. $N=3$ to 5 per group.

Figure 7A:
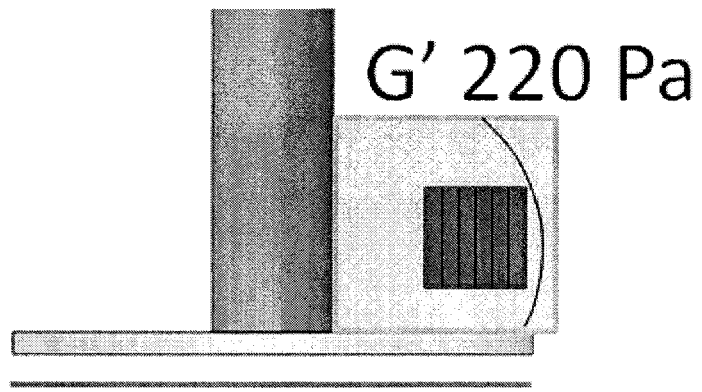
FIGS. 7a and 7b are graphical schematic representations of application of an embodiment of the method of these teachings to anisotropic samples.
Figure 7B:
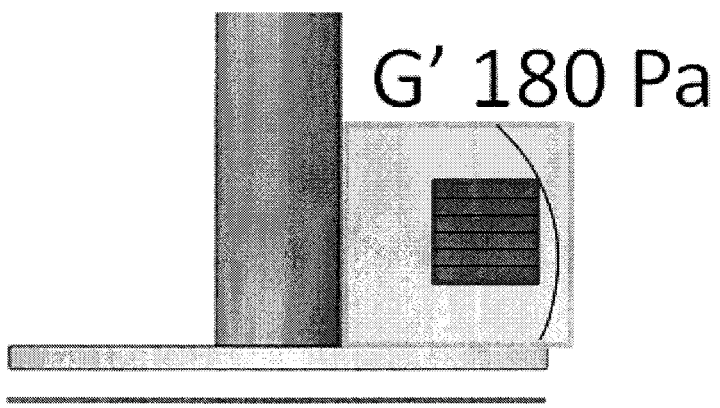

In order to demonstrate the ability to measure anisotropic samples, Cell seeded collagen gels were formed in a 12-well plate with two nylon anchors and then trimmed so that two surfaces were free during culture. After 60 hours, the gel was sliced, removed, and tested in two orthogonal orientations relative to the axis of rotation as depicted in FIGS. 7a and 7b. FIGS. 7a and 7b show schematics of testing of an aligned collagen gel in which the sample is tested at two configurations relative to the axis of rotation demonstrating ability to assess sample anisotropy. FIG. 7a shows results for Sample 'fiber' directions parallel to loading. FIG. 7b shows results for Fiber directions perpendicular to loading.

The above results illustrate that the method of these teachings enables viscoelastic characterization of irregularly shaped and anisotropic samples such as irregularly shaped and anisotropic biological samples.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although the invention has been described with respect to various embodiments, it should be realized these teachings are also capable of a wide variety of further and other embodiments within the spirit and scope of the appended claims.

What is claimed is:

1. A method for viscoelastic characterization of small samples, the method comprising:
   (a) locating a sample so that the sample is radially offset from a center of a sample holding section of a conventional parallel plate rotational rheometer; wherein locating the sample comprises placing the sample on a holding component, the sample being placed so that the sample is radially offset from the center of the sample holding section of the conventional parallel plate rotational rheometer;
   (b) obtaining geometrical and location properties of the sample by obtaining an image of the sample while placed on the holding component;
   (c) obtaining the geometrical and location properties of the sample from the image;
   (d) obtaining, from the geometrical and location properties of the sample, a polar moment of inertia for the sample; and
   (e) obtaining, from a modulus of elasticity obtained from the conventional parallel plate rotational rheometer, using the polar moment of inertia for the sample, a modulus of elasticity for the sample.

2. The method of claim 1 wherein the sample holding component comprises a glass slide.

3. The method of claim 1 wherein the geometrical and location properties comprise position, size and shape.

4. The method of claim 1 wherein the obtaining the modulus of elasticity for the sample comprises adjusting the modulus of elasticity obtained from the conventional parallel plate rotational rheometer by a ratio of a polar moment of inertia for a test sample that occupies the sample holding section of the conventional parallel plate rotational rheometer from the center to an outer radius of a location of the sample to the polar moment of inertia for the sample.

5. The method of claim 1 further comprising repeating steps a) to c) for another orientation of the sample.

6. An apparatus for viscoelastic characterization of small samples, the apparatus comprising:
   a holding component configured such that a sample is radially offset from a center of a sample holding section of a conventional parallel plate rotational rheometer and configured to provide the sample to the conventional parallel plate rotational rheometer;
   an imaging component configured to acquire an image of the sample;
   an analysis component adapted to obtain, from a geometrical and location properties of the sample, a polar moment of inertia for the sample; and
   an adjustment component adapted to obtain, from a modulus of elasticity obtained from the conventional parallel plate rotational rheometer, using the polar moment of inertia for the sample, a modulus of elasticity for the sample.

7. The apparatus of claim 6 wherein the holding component comprises a substantially flat piece of a substantially transparent material dimensioned to be located in the sample holding section of the conventional parallel plate rotational rheometer; and a rod located at substantially the center of substantially flat piece, the rod being adapted to be placed in the sample holding section of the conventional parallel plate rotational rheometer.

8. The apparatus of claim 7 wherein the substantially flat piece comprises an etched portion.

9. The apparatus of claim 6 wherein the imaging component comprises an image acquisition component; and optical components disposed between the sample and the image acquisition component; the optical components being configured to provide an image of the sample to the image acquisition component.

10. The apparatus of claim 9 wherein the optical components comprise a prism disposed to receive an image of the sample and provide the image to the image acquisition component.

11. The apparatus of claim 6 wherein the analysis component comprises:

one or more processors; the one or more processors being operatively connected to the imaging component and receiving an image of the sample from the imaging component; and computer usable media having computer readable code embodied therein, the computer readable code causing the one or more processors to:

obtain the polar moment of inertia for the sample.

12. The apparatus of claim 11 wherein the computer readable code also causes the one or more processors to obtain a radius for a test sample, the radius being obtained from a number of selected locations on a periphery of the image of the sample.

13. The apparatus of claim 12 wherein the one or more processors are operatively connected to an output of the conventional parallel plate rotational rheometer and receive the modulus of elasticity obtained from the conventional parallel plate rotational rheometer; and wherein the computer readable code also causes the one or more processors to:

obtain of the polar moment of inertia for the test sample; and adjust the modulus of elasticity obtained from the conventional parallel plate rotational rheometer by a ratio of the polar moment of inertia for the test sample to the polar moment of inertia for the sample; the computer usable media having the computer readable code and the one or more processors constituting the adjustment component.

* * * * *